United States Patent
Brada

(10) Patent No.: US 12,279,683 B2
(45) Date of Patent: Apr. 22, 2025

(54) SKIN TREATMENT SYSTEM

(71) Applicant: KONINKLIJKE PHILIPS N.V., Eindhoven (NL)

(72) Inventor: Ype Bernardus Brada, Leeuwarden (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 320 days.

(21) Appl. No.: 17/922,863

(22) PCT Filed: May 25, 2021

(86) PCT No.: PCT/EP2021/063772
§ 371 (c)(1),
(2) Date: Nov. 2, 2022

(87) PCT Pub. No.: WO2021/244885
PCT Pub. Date: Dec. 9, 2021

(65) Prior Publication Data
US 2023/0329417 A1    Oct. 19, 2023

(30) Foreign Application Priority Data
Jun. 2, 2020   (EP) ................................... 20177753

(51) Int. Cl.
*A45D 26/00*   (2006.01)
*A61B 5/00*    (2006.01)
*B26B 19/38*   (2006.01)

(52) U.S. Cl.
CPC ........ *A45D 26/0023* (2013.01); *A61B 5/0053* (2013.01); *A61B 5/442* (2013.01); *B26B 19/388* (2013.01)

(58) Field of Classification Search
CPC .. A45D 26/0023; A61B 5/0053; A61B 5/442; A61B 2017/00752; B26B 19/388
See application file for complete search history.

(56) References Cited

U.S. PATENT DOCUMENTS

| | | | |
|---|---|---|---|
| 5,879,312 A | 3/1999 | Imoto | |
| 6,306,148 B1 * | 10/2001 | Knesch | A45D 26/0028 606/133 |
| 2019/0299434 A1 | 10/2019 | Fuerst | |

FOREIGN PATENT DOCUMENTS

| | | |
|---|---|---|
| CN | 204542063 U | 8/2015 |
| EP | 3262971 A1 | 1/2018 |

(Continued)

OTHER PUBLICATIONS

Mechanical Behaviour of Human Skin in Vivo, A Literature Review; F.M. Hendriks; Nat.Lab. Unclassified Report 2001/820; Date of issue: Jul. 2001.

(Continued)

*Primary Examiner* — Tan-Uyen T Ho
*Assistant Examiner* — Khoa Tan Le

(57) ABSTRACT

A skin treatment system (1) comprises a functional member (20) configured to perform a treatment action on skin (2) and to be moved over the skin (2) during operation of the system (1), and a measurement unit (40) including a measurement member (41) configured to be moved over the skin (2) along with the functional member (20) and to be made to indent the skin (2) in the process. The measurement member (41) is displaceable in the measurement unit (40), and the measurement unit (40) is configured to measure a value related to an extent to which the measurement member (41) gets displaced relative to a default position in the measurement unit (40) by action of the skin (2). The measured value corresponds to a measure of an extent to which the skin is indented by the measurement member (41). On the basis of measurement results generated by the measurement unit (40), it is possible to automatically adapt operation of the system (1) to the type of body area under treatment.

15 Claims, 2 Drawing Sheets

(56) References Cited

FOREIGN PATENT DOCUMENTS

| | | |
|---|---|---|
| JP | 2004085548 A | 3/2004 |
| JP | 2009153727 A | 7/2009 |
| JP | 2009240374 A | 10/2009 |
| JP | 2012239779 A | 12/2012 |
| JP | 2012239780 A | 12/2012 |
| KR | 20140145515 A | 12/2014 |
| WO | 2014029509 A1 | 2/2014 |
| WO | 2016096581 A1 | 6/2016 |
| WO | 2017042000 A1 | 3/2017 |
| WO | 2019170497 A1 | 9/2019 |

OTHER PUBLICATIONS

International search report and Written Opinion for patent application No. PCT/EP2021/063772 dated Aug. 17, 2021.

\* cited by examiner

SKIN TREATMENT SYSTEM

CROSS-REFERENCE TO PRIOR APPLICATIONS

This application is the U.S. National Phase application under 35 U.S.C. § 371 of International Application No. PCT/EP2021/063772, filed on May 25, 2021, which claims the benefit of European Patent Application No. 20177753.9, filed on Jun. 2, 2020. These applications are hereby incorporated by reference herein.

FIELD OF THE INVENTION

The invention relates to a skin treatment system comprising a functional member configured to perform a treatment action on skin and to be moved over the skin during operation of the system, and a controller configured to control operation of the skin treatment system.

BACKGROUND OF THE INVENTION

An example of a skin treatment system as mentioned in the opening paragraph is a depilating system that is configured to perform skin treatment in the form of hair removal from skin and that comprises a depilating body as the functional member. According to a conventional design, the depilating body is generally shaped like a cylinder having a circular periphery, wherein the depilating body is rotatable about a rotation axis extending in a longitudinal direction of the depilating body. It is possible for the depilating body to be held in a bent configuration. Further, the depilating body is provided with at least one hair-catching space, wherein the size of the at least one hair-catching space in the longitudinal direction is variable along a periphery of the depilating body or through compression and extension of the depilating body in the longitudinal direction during rotation of the depilating body. Operation of the depilating system for the purpose of removing hair from skin involves driving the depilating body so as to rotate, placing the depilating body on the skin, and letting the depilating body rotate over the skin, so that hair is caught in the at least one hair-catching space as the size of the at least one hair-catching space decreases and is pulled from the skin as the depilating body advances.

Another example of a skin treatment system is a shaving system that is also configured to perform skin treatment in the form of hair removal from skin. As known, a principal difference between shaving and depilation is that hair removal is realized through cutting the hair in the case of shaving and through pulling hair from the skin in the case of depilation. In general, it is practical if a skin treatment system comprises a hand-held appliance and the functional member is integrated in the hand-held appliance.

In the field of skin treatment such as hair removal, it is important to take measures aimed at minimizing undesirable side effects of the treatment such as skin irritation.

U.S. Pat. No. 6,306,148 B1 discloses a sensing means comprising the pivotable swivel arm which detects an angle at which the epilator is placed against the skin. The detected angle is used by an actuating means to modify the closing movement of the clamping elements.

SUMMARY OF THE INVENTION

The invention provides a skin treatment system comprising a functional member configured to perform a treatment action on skin and to be moved over the skin during operation of the system, a controller configured to control operation of the skin treatment system, and a measurement unit including a measurement member configured to be moved over the skin along with the functional member and to be made to indent the skin, wherein the measurement member is displaceable in the measurement unit, and wherein the measurement unit is configured to measure a value related to an extent to which the measurement member gets displaced relative to a default position in the measurement unit by action of the skin, wherein the controller is further configured to receive the measured value from the measurement unit and to use the measured value as a determining factor in an action of determining at least one parameter of operation of the skin treatment system.

It follows from the foregoing definition that the skin treatment system according to the invention comprises a measurement unit besides the functional member and the controller, wherein the measurement unit includes a measurement member that is displaceable in the measurement unit and that serves to indent the skin. During operation of the skin treatment system, the measurement unit measures a value related to an extent to which the measurement member gets displaced relative to a default position in the measurement unit by action of the skin, which is a measure of an extent to which the skin is indented by the measurement member. Input obtained from the measurement unit is used by the controller in a process of determining at least one parameter of operation of the skin treatment system. The functional member and the measurement unit may be integrated in a hand-held appliance, in which case the controller may be a remote unit located outside of the hand-held appliance, which does not alter the fact that other options are covered by the invention as well. In respect of the option of the skin treatment system comprising a hand-held appliance it is further noted that it may be so that the functional member is moveable in the hand-held appliance, and that the at least one parameter of operation of the skin treatment system determined by the controller may comprise at least one control setting of the functional member related to movement of the functional member in the hand-held appliance in that case. The treatment action on the skin may be one of hair removal through depilation and hair removal through shaving, for example, wherein it is to be noted that the invention is not restricted to a particular type of skin treatment in any way.

According to a first practical example, the at least one parameter of operation of the skin treatment system determined by the controller comprises at least one control setting of the functional member.

In the context of a skin treatment system, in order to achieve optimal results of the skin treatment while achieving minimal side effects such as skin irritation at the same time, it is desirable to have a real-time indication of which body area is subjected to treatment during operation of the system. Such an indication could then be applied to automatically adapt at least one control setting of the functional member to actual circumstances and avoid a situation in which a user is requested to choose an operation mode of the system in relation to the body area that is or will be treated. For example, in the practical case of the skin treatment system comprising a hand-held appliance and the functional member being moveable in the hand-held appliance, it may be advantageous to set the speed of movement of the functional member at a lower value when sensitive body areas such as the facial area or the armpits are subjected to a skin treatment action, and to set the speed of movement of the functional member at a higher value when less sensitive body areas such as the legs or the arms are subjected to the skin treatment action.

According to an insight underlying the invention, different body areas involve different skin stiffness, and the extent to which the measurement member gets displaced relative to a default position in the measurement unit by action of the skin is related to the skin stiffness. In view thereof, it is found that the measured value is representative of the body area that is subjected to the skin treatment action during operation of the skin treatment system, so that the measured value is suitable to be used for the purpose of determining at least one control setting of the functional member. When the invention is put to practice, there is no need for performing a separate action for assessing the actual type of body area or for requesting a user to provide an indication in this respect, because relevant measurement results are automatically obtained during a skin treatment action. This does not alter the fact that the invention does not exclude an option of the measurement unit being equipped with an accelerometer or another type of positioning sensing device besides the measurement member for the purpose of increasing accuracy of the process of determining at least one control setting of the functional member as based on assumptions about the body area on which the skin treatment action is performed. Having a positioning sensing device also offers a possibility of assessing whether the measurement member is placed correctly on the skin and providing appropriate feedback in this respect to a user.

According to a second practical example, the skin treatment system comprises a user output interface such as a display device, and the at least one parameter of operation of the skin treatment system determined by the controller comprises at least one control setting of the user output interface. Thus, besides the potential to automatically adapt the way in which the functional member is controlled to the body area that is subjected to the skin treatment action, the invention has the potential to provide relevant information to a person such as the user of the skin treatment system by controlling a user output interface as a means configured to convey information to a person, as an alternative functionality or as an additional functionality. Examples of relevant information include information about a determined body area so that a user may assess whether the information is correct, and skin condition-related information such as information about skin stiffness.

Preferably, the measurement member is shaped such and comprises such material that at the position of contact to the skin, a coefficient of friction between the measurement member and the skin is as low as possible. In this way, stretching of the skin as the measurement member is dragged along the skin is minimized, so that influence of the dragging movement of the measurement member on the tension in the skin is minimized and the measurement results can be accurate.

In the framework of the invention, various options are applicable when it comes to the configuration of the measurement unit. For example, it is practical if the measurement member is mounted in the measurement unit in a resilient fashion, which may be through a spring arrangement, wherein the spring arrangement may comprise a coil spring acting on the measurement member. A spring arrangement is useful in setting the default position of the measurement member in the measurement unit. Sensitivity of the measurement unit can be determined by a defined spring constant of the spring arrangement, and a threshold of the measurement unit can be determined by pretension of the spring arrangement. If a force exerted on the measurement member is so low that the pretension of the spring arrangement is not counteracted, the measurement member will not be made to move away from the default position. Preferably, the value of the pretension of the spring arrangement is chosen such that having the measurement member at the default position can be taken as an indication that there is no situation in which skin is contacted and in which measurements should be performed, i.e. is chosen so as to be low enough that even skin of low stiffness will be able to push the measurement member from the default position.

It is practical if the measurement unit further includes a reference member that is configured to be moved over the skin along with the functional member and the measurement member and to contact the skin in the process, wherein the measurement member and the reference member are movable relative to each other. The reference member can have a function of guiding the measurement member, in which case it may be practical if the reference member comprises a hollow cylinder element that is arranged to surround at least a portion of the measurement member. In any case, the reference member provides a support on the skin while the measurement member is allowed to indent the skin to an extent that is determined by predetermined constructional features following from the way in which the measurement member is mounted in the measurement unit on the one hand, and the variable skin stiffness on the other hand.

It may be so that the reference member is fixed in the measurement unit, but it is also possible that the reference member is displaceable in the measurement unit. In the latter case, it is practical if the reference member is mounted in the measurement unit in a resilient fashion, which may be through a spring arrangement, wherein optionally the spring arrangement through which the reference member is mounted in the measurement unit is arranged in series in the measurement unit with the spring arrangement through which the measurement member is mounted in the measurement unit. An advantage of the latter case is that an influence of user handling is minimized, as having a displaceable arrangement of the reference member in the measurement unit allows for pressing the reference member to the skin at a predefined force.

In the case that the reference member is fixed in the measurement unit, the default position of the measurement member in the measurement unit is a position relative to a fixed component of the measurement unit, and in the case that the reference member is displaceable in the measurement unit, the default position of the measurement member in the measurement unit is a position relative to a displaceable component of the measurement unit.

For the purpose of enabling the measurement unit to measure the intended value related to displacement of the measurement member, it is practical if the measurement unit further includes a sensor arrangement configured to detect a position of the measurement member in the measurement unit. The fact is that each position which is different from the default position represents a displacement of the measurement member. In a practical embodiment, the sensor arrangement may include a combination of a magnet and a Hall Effect sensor, which does not alter the fact that other embodiments of the sensor arrangement are feasible, particularly embodiments which allow for performing measurements in ranges of millimeters. For example, the sensor arrangement may be configured to detect the position of the measurement member in the measurement unit through at least one of LVDT (Linear Variable Differential Transformer) sensing, capacitive sensing, Eddy-current sensing, ultrasonic sensing and optical sensing.

As mentioned in the foregoing, the invention provides a possibility of automatically adjusting the way in which the functional member of the skin treatment system is operated. For example, in the case of the skin treatment system being a depilating system, the at least one control setting of the functional member that is determined by the controller may be a control setting through which a certain rotation speed of the depilating body can be obtained. Generally speaking, in such a case, a method of control of operation of the depilating system may be realized according to which the rotation speed of the depilating body is reduced when the depilating action is performed on a sensitive body area. According to another feasible option, the at least one control setting of the functional member may be a control setting through which an extent to which the depilating body is extended relative to a housing portion or the like supporting the depilating body is determined. Generally speaking, in such a case, a method of control of operation of the depilating system may be realized according to which the depilating body is further retracted relative to the housing portion when the measurement results are indicative of a sensitive body area.

The above-described and other aspects of the invention will be apparent from and elucidated with reference to the following detailed description of a depilating system comprising a measurement unit, wherein various possibilities in respect of the configuration of the measurement unit and components thereof are addressed.

BRIEF DESCRIPTION OF THE DRAWINGS

The invention will now be explained in greater detail with reference to the figures, in which equal or similar parts are indicated by the same reference signs, and in which.

DETAILED DESCRIPTION OF THE EMBODIMENTS

Figure 1:
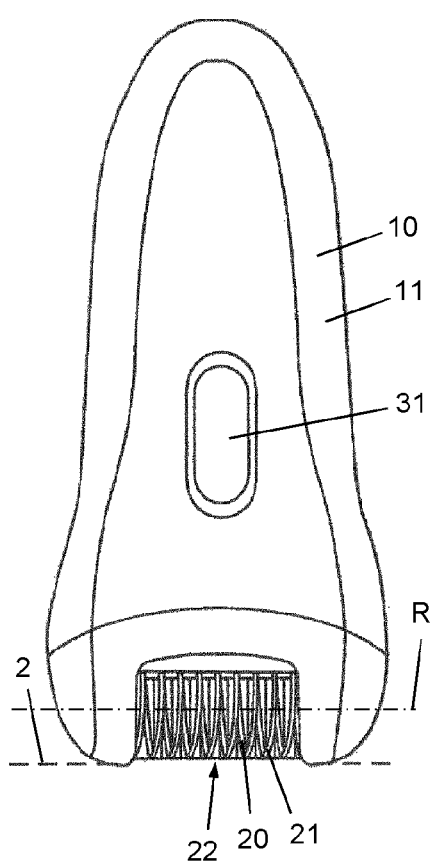
FIG. 1 diagrammatically shows a front view of a handheld depilating device that is part of a depilating system according to an embodiment of the invention, FIG. 2 diagrammatically shows components of the depilating system, namely a depilating body, a housing portion supporting the depilating body, a measurement unit, a controller and a display device of the depilating system.

In the following, various features of a depilating system 1 according to an embodiment of the invention will be described, wherein it is noted that the depilating system 1 is just one example of many types of skin treatment systems which are feasible in the framework of the invention. With reference to FIG. 1, it is further noted that it is practical if the depilating system 1 comprises a hand-held appliance 10 including a housing 11 for accommodating a number of components of the depilating system 1. By having the hand-held appliance 10, convenient use of the depilating system 1 on various body areas including face, armpits, arms and legs is enabled.

The depilating system 1 is configured to be used for the purpose of performing a hair removing operation on skin. In view thereof, the depilating system 1 comprises a depilating body 20 which is intended to actually interact with hair to be plucked from the skin. For the purpose of catching and clamping the hair, the depilating body 20 has hair-clamping members 21 with hair-catching spaces 22 between them. In the shown example, the depilating body 20 is generally shaped like a cylinder having a circular periphery, wherein the depilating body 20 is rotatable about a rotation axis R extending in a longitudinal direction of the depilating body 20. The size of the hair-catching spaces 22 in the longitudinal direction is variable along a periphery of the depilating body 20. It will be understood that the depilating system 1 comprises components such as a driving mechanism (not shown) for driving the depilating body 20 so as to actually perform a rotational movement about the rotation axis R during operation of the depilating system 1 and an electric supply arrangement (not shown) such as a (rechargeable) battery in case the hand-held appliance 10 is cordless.

Figure 2:
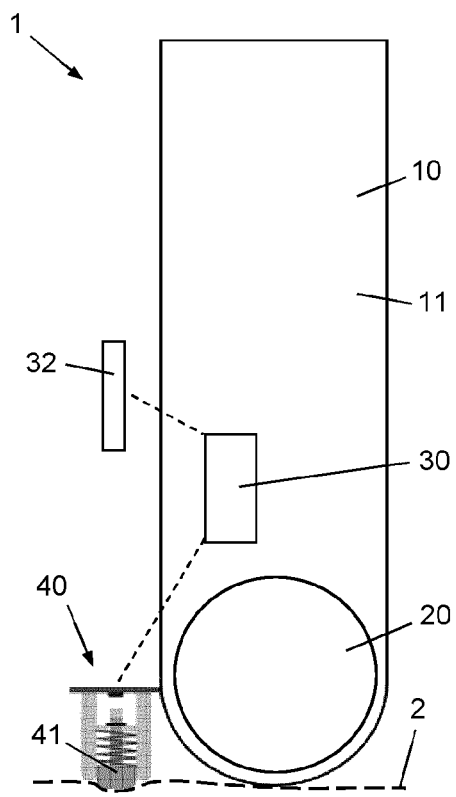

As can be seen in FIG. 2, it is practical if the depilating system 1 further comprises a controller 30 that is configured to control operation of the depilating system 1. For the purpose of allowing a user to activate and deactivate the depilating system 1, and possibly also to choose a mode of operation of the depilating system 1, a suitable user input interface 31 such as a button may be provided on the housing 11 of the hand-held appliance 10. When the depilating system 1 is activated, the depilating body 20 is driven so as to rotate. Skin 2 to be subjected to a depilating action by means of the depilating system 1 is diagrammatically indicated in the figures by means of a dashed line. Proper use of the depilating system 1 involves having the depilating system 1 in the activated state and handling the hand-held appliance 10 in such a way that the depilating body 20 rotates over the skin 2. In the process, hair is caught in the hair-catching spaces 22 of the depilating body 20 and is pulled from the skin 2 as the depilating body 20 advances.

FIG. 2 illustrates that the depilating system 1 further comprises a measurement unit 40. The measurement unit 40 includes a probe-like measurement member 41 that is configured to be moved over the skin 2 along with the depilating body 20 and to be made to indent the skin 2 in the process, and that is displaceable in the measurement unit 40, which means that the measurement member 41 is displaceable in the hand-held appliance 10. Constructional details of the measurement unit 40 will be explained later in more detail with reference to FIGS. 3 and 4. The measurement unit 40 serves for measuring a value related to an extent to which the measurement member 41 gets displaced relative to a default position in the measurement unit 40 by action of the skin 2. A desire to automatically adjust at least one control setting of the depilating body 20 in view of the body area that is subjected to a depilating action may be at the basis of this functionality of the measurement unit 40, taking into account the fact that one body area is more sensitive than another body area. In this respect, it is further noted that an extent to which the skin 2 gets indented by means of the measurement member 41 is indicative of skin stiffness, and that skin stiffness is indicative of the body area. Hence, it is advantageous if the measurement unit 40 outputs a measured value to the controller 30 during operation of the depilating system 1, and if the controller 30 functions to determine at least one control setting of the depilating body 20, wherein the controller 30 takes the measured value as a determining factor in the process. For example, if the measured value is indicative of a body area that is known as being sensitive, the controller 30 may provide output aimed at setting a relatively low value of a rotation speed of the depilating body 20.

Further, as shown in FIG. 2, the depilating system 1 may be equipped with a display device 32 as a user output interface, wherein it is practical if the controller 30 is further configured to provide output representative of the skin stiffness and/or the determined body area and/or one or more possible other types of information to the display device 32 so that a user may be informed through the display device 32, and may be allowed to check whether the depilating system 1 functions properly, for example.

The controller 30 may be configured in any suitable way for determining appropriate output such as at least one control setting of the depilating body 20 or at least one control setting of the display device 32. For example, it is possible that the controller 30 is configured to check whether the measured value is above or below a predetermined threshold value in order to choose an appropriate one of two possible control settings of at least one component of the depilating system 1, or to determine an appropriate control setting by means of a look-up table. In any case, an important advantage of the invention resides in the fact that the measurement allowing for adaptation of operation of the depilating body 20 to the type of body area under treatment and/or control of a display device 32 so as to provide relevant information to a person and/or influencing the functioning of one or more other components of the depilating system 1 can be performed during a depilating action so that it is not necessary to perform a separate measurement.

Exchange of signals between the controller 30 and the display device 32, and between the controller 30 and the measurement unit 40, respectively, is indicated by means of dashed lines in FIG. 2. The measurement unit 40 can be located at any position relative to the depilating body 20 on the basis of which a position of the measurement unit 40 is obtained in which the measurement unit 40 is enabled to properly perform measurements during use of the hand-held appliance 10 on the skin 2, wherein it may be advantageous to have a more or less central position of the measurement unit 40, particularly the measurement member 41, on the hand-held appliance 10.

Figure 3:
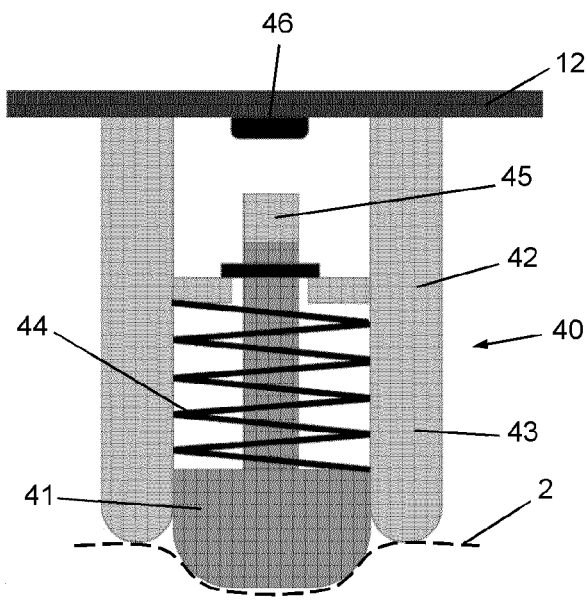
FIG. 3 illustrates a first possible configuration of the measurement unit.

With reference to FIG. 3, details of a first option in respect of the configuration of the measurement unit 40 will now be elucidated. Besides the measurement member 41, the measurement unit 40 comprises a reference member 42 that, similar to the measurement member 41, is configured to be moved over the skin 2 along with the depilating body 20 and to contact the skin 2 in the process. In the first embodiment of the measurement unit 40, the reference member 42 is fixed in the measurement unit 40, which means that the reference member 42 is fixed in the hand-held appliance 10. In this respect, it is shown in FIG. 3 that the reference member 42 is fixedly connected to a portion 12 of the housing 11 of the hand-held appliance 10. The reference member 42 comprises a hollow cylinder element 43 that is arranged to surround at least a portion of the measurement member 41, and the measurement member 41 is mounted in the reference member 42 through a spring arrangement 44 that comprises a coil spring in the shown example. Further, at an end of the measurement member 41 that is opposite to an end configured to contact the skin 2, the measurement member 41 is equipped with a magnet 45, wherein the measurement unit 40 further comprises a Hall Effect sensor 46 that is located at a position for facing the magnet 45.

During operation of the depilating system 1, the hand-held appliance 10 is moved over the skin 2 by a user. The depilating body 20 is driven so as to rotate and thereby performs the depilating action as intended. Both the measurement member 41 and the reference member 42 are dragged along the skin 2 in the process. Preferably, both the measurement member 41 and the reference member 42 are designed such that an as low as possible coefficient of friction prevails between the measurement member 41 and the skin 2 and between the reference member 42 and the skin 2, respectively. Among other things, this can be realized on the basis of the shape of the respective ends of the measurement member 41 and the reference member 42, by choosing rounded shapes for example, and on the basis of the material of the measurement member 41 and the reference member 42 at the position of the respective ends. Due to the low friction between the skin 2 and the measurement member 41 and the reference member 42, stretching of the skin 2 as a result of the measurement member 41 and the reference member 42 being dragged along the skin 2 only takes place to a minimal extent. As a result, tension in the skin 2 is minimized, so that it is safe to assume that the measurement results to be obtained by means of the measurement unit 40 follow directly from indentation of the skin 2 by means of the measurement member 41 in a longitudinal direction of the measurement member 41, and are not influenced by mechanical effects taking place in a direction along the skin 2 due to the dragging movement of the measurement member 41 and the reference member 42 along the skin 2. Otherwise, measurement results would be obtained which are related to a skin stiffness that is increased due to increased tension in the skin 2.

The measurement member 41 is mounted in the measurement unit 40 in such a way that a default position of the measurement member 41 is a position of causing indentation of the skin 2. The spring constant of the spring arrangement 44 acting on the measurement member 41 determines sensitivity of the measurement unit 40, and a pretension of the spring arrangement 44 determines a threshold of the measurement unit 40, i.e. the point at which the measurement member 41 can be moved out of the default position and measurement results can be obtained. Preferably, the pretension of the spring arrangement 44 is high enough for preventing generation of measurement results in a situation in which there is no contact to the skin 2. It will be understood that in a case of the skin 2 having high stiffness, the indentation of the skin 2 by means of the measurement member 41 will be less than in a case of the skin 2 having low stiffness. This means that in the first case, the measurement member 41 will be at a more retracted position in the measurement unit 40 than in the latter case, and this also means that in the first case, the magnet 45 will be closer to the Hall Effect sensor 46 than in the latter case. The Hall Effect sensor 46 outputs a signal that is representative of the position of the measurement member 41 and thereby of a displacement of the measurement member 41 relative to the default position, which is received by the controller 30 and taken into account in a process of determining at least one parameter of operation of the depilating system 1.

Generally speaking, the depth of the indentation of the skin 2 is a function of the (non-linear) stiffness of the skin 2, the stiffness of the spring arrangement 44, and the diameter and the shape of the measurement member 41 at the position of contact to the skin 2. As the stiffness of the skin 2 is the only variable factor, it follows that the indentation depth of the skin 2 is representative of the stiffness of the skin 2, indeed, and that it is appropriate to measure displacement of the measurement member 41 as this factor is a direct measure of the indentation depth.

Figure 4:
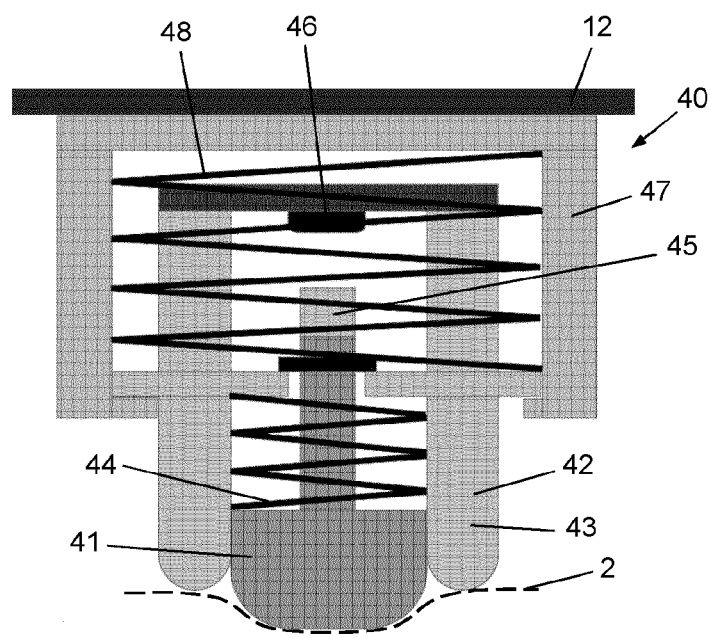
FIG. 4 illustrates a second possible configuration of the measurement unit.

With reference to FIG. 4, details of a second option in respect of the configuration of the measurement unit 40 will now be elucidated. The second embodiment of the measurement unit 40 resembles the first embodiment of the measurement unit 40 to a large extent, and in view thereof, the explanation of the constructional and functional features of the first embodiment of the measurement unit 40 is equally applicable to the second embodiment of the measurement unit 40, with the exception of the remark that the reference member 42 is fixed in the measurement unit 40. The fact is that in the second embodiment of the measurement unit 40, the reference member 42 is displaceable in the measurement unit 40, which means that the reference member 42 is displaceable in the hand-held appliance 10. The reference member 42 is mounted to a holder 47 of the measurement unit 40 through a spring arrangement 48 that comprises a coil spring in the shown example. Thus, in the second embodiment of the measurement unit 40, the reference member 42 is mounted in the measurement unit 40 through a spring arrangement 48, and the measurement member 41 is mounted in the movably arranged reference member 42 through a spring arrangement 44, wherein it is noted that the respective spring arrangements 44, 48 are arranged in series in the shown example.

Like the spring arrangement 44 mounting the measurement member 41, the spring arrangement 48 mounting the reference member 42 has a defined spring constant and a defined pretension. The spring mounting of the reference member 42 is meant to make the measurements to be performed by the measurement unit 40 more robust, i.e. less sensitive to user handling. The fact is that on the basis of the spring mounting of the reference member 42, it is achieved that the reference member 42 is pressed with a defined force to the skin 2, practically independent from pressing forces applied by the user.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details which are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The terms "comprise" and "include" as used in this text will be understood by a person skilled in the art as covering the term "consist of". Hence, the term "comprise" or "include" may in respect of an embodiment mean "consist of", but may in another embodiment mean "contain/have/be equipped with at least the defined species and optionally one or more other species".

Notable aspects of the invention are summarized as follows. A skin treatment system 1 such as a depilating system comprises a functional member 20 that is configured to perform a treatment action on skin 2 and to be moved over the skin 2 during operation of the system 1, and a measurement unit 40 including a measurement member 41 that is configured to be moved over the skin 2 along with the functional member 20 and to be made to indent the skin 2 in the process. The measurement member 41 is displaceable in the measurement unit 40, and the measurement unit 40 is configured to measure a value related to an extent to which the measurement member 41 gets displaced relative to a default position in the measurement unit 40 by action of the skin 2. On the basis of measurement results generated by the measurement unit 40, it is possible to enable actions such as automatically adapting operation of the skin treatment system 1 to the type of body area under treatment and providing skin condition-related information to a user of the system 1.

The invention claimed is:

1. Skin treatment system, comprising:
a functional member configured to perform a treatment action on skin and to be moved over the skin during operation of the system,
a controller configured to control operation of the skin treatment system, and
a measurement unit including a measurement member configured to be moved over the skin along with the functional member and to be made to indent the skin in the process, wherein the measurement member is displaceable in the measurement unit, and wherein the measurement unit is configured to measure a value related to an extent to which the measurement member gets displaced relative to a default position in the measurement unit by action of the skin,
wherein the controller is further configured to receive the measured value from the measurement unit and to use the measured value as a determining factor in an action of determining at least one parameter of operation of the skin treatment system, characterized in that:
the measured value corresponds to a measure of an extent to which the skin is indented by the measurement member.

2. Skin treatment system according to claim 1, wherein the at least one parameter of operation of the skin treatment system determined by the controller (30) comprises at least one control setting of the functional member.

3. Skin treatment system according to claim 1, further comprising a user output interface, wherein the at least one parameter of operation of the skin treatment system determined by the controller comprises at least one control setting of the user output interface.

4. Skin treatment system according to claim 1, wherein the measurement member is mounted in the measurement unit through a spring arrangement.

5. Skin treatment system according to claim 1, wherein the measurement unit further includes a reference member configured to be moved over the skin along with the functional member and the measurement member and to contact the skin in the process, and wherein the measurement member and the reference member are movable relative to each other.

6. Skin treatment system according to claim 5, wherein the reference member is fixed in the measurement unit.

7. Skin treatment system according to claim 5, wherein the reference member is displaceable in the measurement unit.

8. Skin treatment system according to claim 7, wherein the reference member is mounted in the measurement unit through a spring arrangement.

9. Skin treatment system according to claim 8 insofar as dependent on claim 4, wherein the spring arrangement through which the reference member is mounted in the measurement unit is arranged in series in the measurement unit with the spring arrangement through which the measurement member is mounted in the measurement unit.

10. Skin treatment system according to claim 5, wherein the reference member comprises a hollow cylinder element that is arranged to surround at least a portion of the measurement member.

11. Skin treatment system according to claim 1, wherein the measurement unit further includes a sensor arrangement configured to detect a position of the measurement member in the measurement unit.

12. Skin treatment system according to claim 11, wherein the sensor arrangement includes a combination of a magnet and a Hall Effect sensor.

13. Skin treatment system according to claim 11, wherein the sensor arrangement is configured to detect the position of the measurement member in the measurement unit through at least one of LVDT (Linear Variable Differential Transformer) sensing, capacitive sensing, Eddy-current sensing, ultrasonic sensing and optical sensing.

14. Skin treatment system according to claim 1, wherein the treatment action on skin is a hair removal action.

15. Skin treatment system according to claim 1, wherein at least the functional member and the measurement unit are integrated in a hand-held appliance, wherein the functional member is moveable in the hand-held appliance, and wherein the at least one parameter of operation of the skin treatment system determined by the controller comprises at least one control setting of the functional member related to movement of the functional member in the hand-held appliance.

* * * * *